United States Patent [19]
Hirotsu et al.

[11] Patent Number: 4,662,875
[45] Date of Patent: May 5, 1987

[54] ABSORBENT ARTICLE

[75] Inventors: Dennis O. Hirotsu, Cincinnati, Ohio; Anthony J. Robertson, Madison, Wis.

[73] Assignee: The Procter & Gamble Company, Cincinnati, Ohio

[21] Appl. No.: 802,803

[22] Filed: Nov. 27, 1985

[51] Int. Cl.⁴ .............................................. A61F 13/16
[52] U.S. Cl. ..................................................... 604/389
[58] Field of Search ............... 604/389, 390, 391, 394, 604/396, 385.1; 128/DIG. 15, 165, 169

[56] References Cited

U.S. PATENT DOCUMENTS

| | | | |
|---|---|---|---|
| 3,081,772 | 3/1963 | Brooks et al. | 128/287 |
| 3,638,651 | 2/1972 | Torr | 604/390 |
| 3,646,937 | 3/1972 | Gellert | 604/390 |
| 3,856,008 | 12/1974 | Fowler et al. | 128/DIG. 15 |
| 3,869,761 | 3/1975 | Schaar | 604/390 |
| 4,036,233 | 7/1977 | Kozak | 128/287 |

FOREIGN PATENT DOCUMENTS

| | | | |
|---|---|---|---|
| 2122164 | 11/1972 | Fed. Rep. of Germany | 604/389 |
| 1263391 | 12/1961 | France | 128/169 |

*Primary Examiner*—John D. Yasko
*Attorney, Agent, or Firm*—John M. Pollaro; Fredrick H. Braun; Richard C. Witte

[57] ABSTRACT

An absorbent article, such as a disposable diaper or an incontinent brief having indicia means provided for aiding an individual fitting the article to a wearer to obtain optimal waist fit and leg opening fit. Indicia means are provided in an area at least coextensive with a part of an area to which fastening means are affixed to the article when the article is fitted to a wearer. Indicia, as used herein are any type of lines, patterns, ornamental designs, symbols, script, color codes, or other markings which have the capability, either inherently or with additional denotation, to aid an individual fitting the article to promptly locate a desired affixation point for a particular fastening means.

18 Claims, 3 Drawing Figures

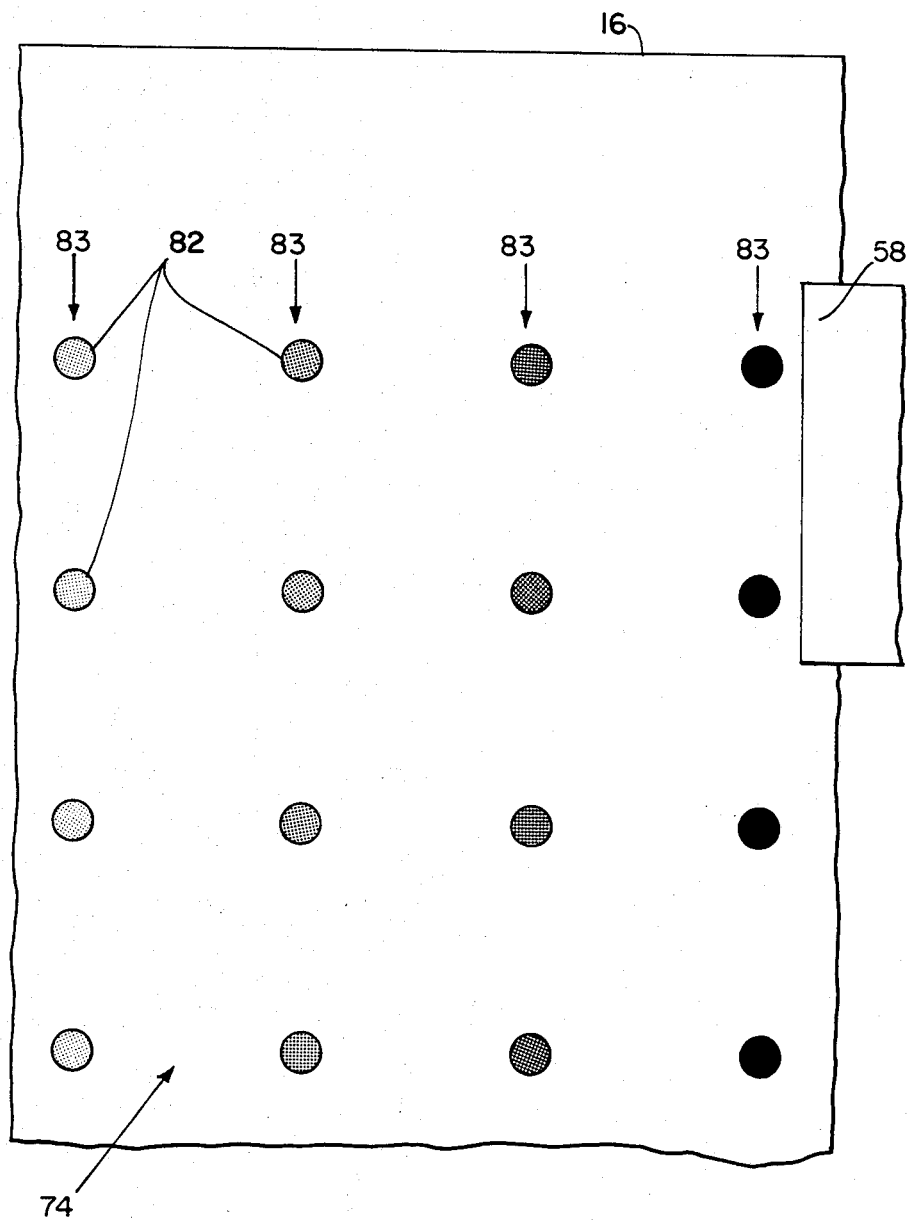

ABSORBENT ARTICLE

BACKGROUND OF THE INVENTION

This invention relates to absorbent articles, such as disposable diapers or incontinent briefs. More particularly, this invention relates to such absorbent articles having means for consistently improved fit.

Absorbent articles, such as disposable diapers, are well known articles of manufacture which are worn by infants and incontinent persons. Absorbent articles are worn about the lower torso and are intended to absorb and contain urine and feces thereby preventing the urine and feces from soiling, wetting, or otherwise contaminating the articles (e.g., clothing, bedding, etc.) which come into contact with the absorbent article wearer.

In general, disposable diapers all have the same basic structure which comprises an absorbent core encased between a liquid permeable user contacting topsheet, a liquid impermeable backsheet and means for fastening the diaper about the wearer's waist. When fitting an absorbent article to a wearer the article is fastened about the wearer's waist thereby effecting a waist closure. Fitting the absorbent article about the wearer usually requires the front and back waist portions of the diaper to overlap each other. The prior art teaches numerous variations of fastening means. Diapers are generally provided with at least first and second fastening means, each fastening means being disposed to effect waist closure on each respective side of the wearer's waist. Most often, the means for fastening the diaper about the wearer's waist will be adhesive tape tabs.

The amount of overlap on each side of the diaper will affect the fit about the wearer's waist and the size of the leg opening on each side of the diaper corresponding to that respective overlap. Proper fit about the waist and each leg opening is vital for optimal diaper performance in terms of minimum leakage in the waist and leg opening areas. One problem commonly encountered when fitting the diaper, especially in the case of infants, is that the wearer's do not cooperate with the individual fitting of the diaper. In more specific terms, the wearer may kick, wave his or her arms, attempt to roll over and perform other assorted movements and actions which have the effect of making it difficult for the individual fitting the diaper to coordinate proper waist fit with proper leg fit at each leg opening. Another problem is that means are not provided on prior diapers which enable an individual fitting the diaper to affix the fastening means to precise, desired locations or to affix the fastening means at the same locations for subsequently fitted diapers. The individual fitting the diaper is, therefore, faced with a variety of difficulties when affixing the fastening means to the optimal positions for proper fit.

First, due to the actions of the intended wearer and the lack of a means for guiding placement of the fastening tabs, it is difficult to affix any of the fastening means to effect waist closure at positions which facilitate good leg opening fit and/or proper waist fit. When the first fastening means is not fastened to the diaper at the proper location the leg opening corresponding to the side of the diaper of the first fastening means will necessarily have improper fit. When the first fastening means is fastened at an improper location, the second fastening means can be affixed through trial and error to optimize either waist fit or leg opening fit for the leg opening on the side of the diaper corresponding to the second fastening means. However, the second fastening means cannot thereafter be affixed at a position to provide both good waist fit and proper leg opening fit for the respective leg opening. Thus, either waist fit or second leg opening fit will generally necessarily be improper as a result of improper first fastening means positioning.

A second problem is that even when the first fastening means is affixed to the diaper at the ideal location for coordinating proper waist and leg opening fit, it is still difficult to affix the second fastening means to the corresponding ideal location for proper waist and leg opening fit. Such difficulty also arises from actions of the wearer and a lack of means for guiding placement of the fastening tabs. An improperly positioned second fastening means, in such circumstances, will lead to waist fit that is either too tight or too loose and leg opening fit respective to the second fastening means that is correspondingly either too tight or too loose.

A third problem is that even when proper fit is obtained for a particular diaper, it is difficult to repeat such fit for subsequently fitted diapers since the problems previously discussed may be reexperienced for each subsequent fitting.

It is an object of this invention to provide an absorbent article having means for facilitating both proper fit about a wearer's waist and proper leg opening fit for each of a wearer's legs.

It is another object of this invention to provide an absorbent article having means for coordinating proper leg opening fit for each absorbent leg opening with proper waist fit.

It is also an object to provide an absorbent article having means for facilitating proper fit about the wearer's waist and legs on a consistent basis for subsequently fitted absorbent articles.

These and other objects of the invention will become apparent when considered in view of the following description and the drawings.

SUMMARY OF THE INVENTION

According to the present invention, an absorbent article, such as a disposable diaper or an incontinent brief, is provided with indicia means for aiding an individual fitting the article to a wearer to obtain optimal waist fit and leg opening fit. The article comprises: a first region having a first laterally spaced portion and a second laterally spaced portion; a second region connected to said first region; fastening means for fastening said first laterally spaced portion of said first region to said second region at a first attachment area; fastening means for fastening said second laterally spaced portion of said first region to said second region at a second attachment area; indicia means coextensive with at least a part of said first attachment area; and indicia means coextensive with at least a part of said second attachment area; said indicia means providing guidance in fitting said article to a wearer. The indicia are located in areas corresponding to the areas at which the fastening means are affixed when the article is in the configuration it assumes when fitted to a wearer.

Indicia, as used herein are any type of lines, patterns, ornamental designs, symbols, script, color codes, or other markings which have the capability, either inherently or with additional denotation, to aid an individual fitting the article to promptly locate a desired affixation point for a particular fastening means.

The indicia enable an individual fitting an absorbent article to a wearer to, with experience, identify optimum position for affixing each of the fastening means and effecting waist closure. The indicia also enable the individual fitting the absorbent article to provide the wearer with consistent fit for subsequently fitted absorbent articles. Significantly, the indicia enable the diaper to be consistently fitted in a manner such that the waist fit and leg opening fit of each absorbent article are coordinated to provide the best overall fit.

In practice, an individual fitting the article to a wearer would first affix at least one fastening means to one side of the centerline of the article. The individual, with the aid of the indicia, would ascertain the geographic location optimally chosen for good fit with the aid of corresponding indicia coextensive the second attachment area. The article therefore, with the aid of the indicia, may be properly fitted to the wearer. Occurrences of leakage due to improper fit may therefore reduced to the design limits of the particular absorbent article. Additionally occurrences of irritation to the wearer due to excessively tight fit may also be reduced with the aid of the indicia of the present invention.

BRIEF DESCRIPTION OF THE DRAWINGS

FIG. 3 is an expanded frontal view of a set of indicia.

DESCRIPTION OF PREFERRED EMBODIMENTS

Figure 1:
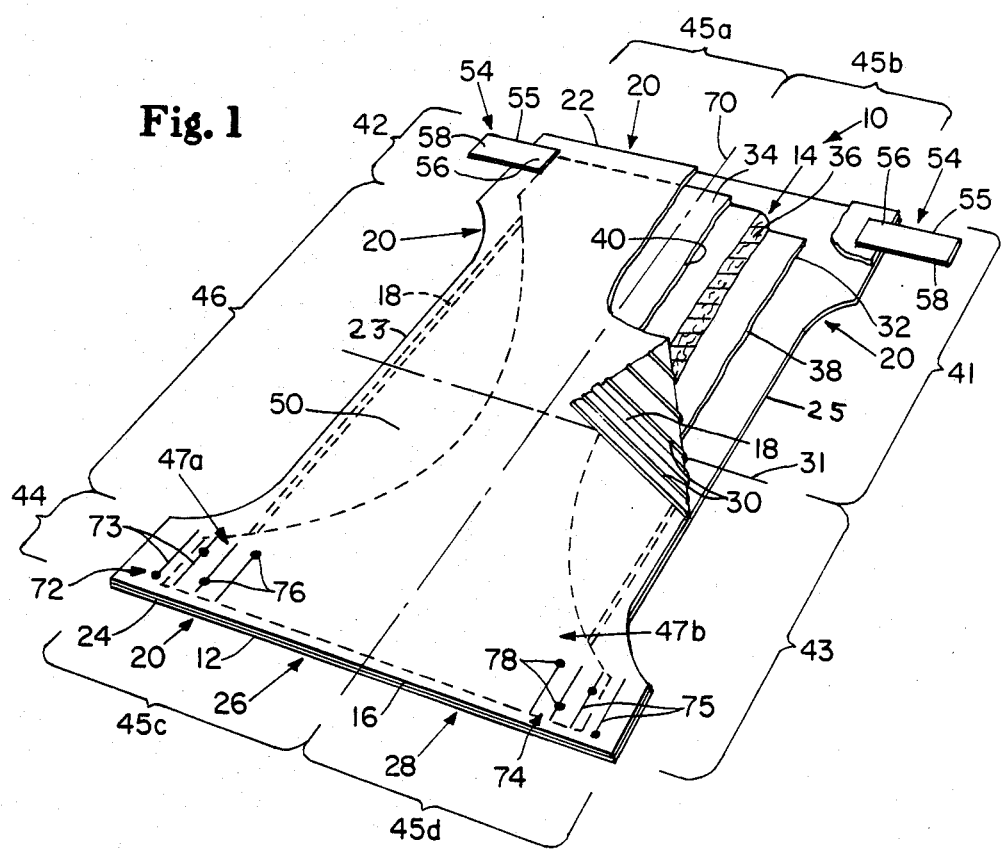
FIG. 1 is a partially cutaway perspective view of a disposable diaper incorporating the present invention.

Referring now to the drawings, there is shown a preferred embodiment of the present invention as it would be used in a disposable diaper intended to be worn by an infant. As used herein, the term "disposable diaper" refers to a garment generally worn by infants or incontinent persons, which is drawn up between the legs and fastened about the waist of the wearer and further, which is intended to be discarded after a single use (i.e., it is not intended to be laundered or otherwise restored and reused).

FIG. 1 is a partially cut away perspective view of the disposable diaper 10 of the present invention prior to its being folded and placed on the diaper wearer by the diaper user. As can be seen in FIG. 1, a preferred diaper 10 basically comprises a liquid impermeable topsheet 12, an absorbent means 14, a liquid impermeable backsheet 16 and elastic member 18. While the topsheet 12, absorbent means 14, liquid impermeable backsheet 16, and elastic member 18 may be assembled in a variety of well known configurations, a preferred disposable diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

Figure 2:
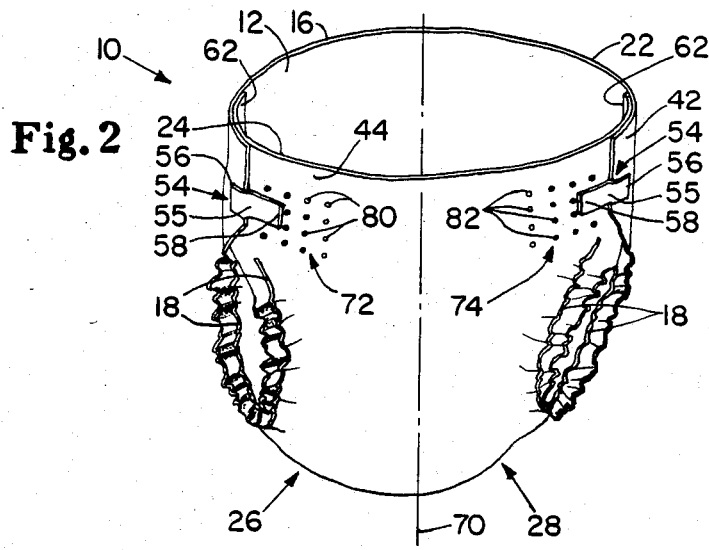
FIG. 2 is a frontal view showing a disposable diaper incorporating the present invention, wherein the diaper is in a configuration which it would assume when fitted to a wearer.

FIGS. 1 and 2 show a preferred embodiment of the diaper 10 in which the topsheet 12 and the backsheet 16 are coextensive and have length and width dimensions generally larger than those of the absorbent means 14. The topsheet 12 is superimposed on the backsheet 16 thereby forming a periphery 20 of diaper 10. The periphery 20 defines the outer periphery or, in other words, the outer extent of the diaper 10. The periphery 20 comprises first end 22, second end 24, first longitudinal edge 23, and second longitudinal edge 25.

The topsheet 12 may be affixed to the backsheet 16 in any suitable manner as is well known in the diaper manufacturing art. In a preferred embodiment, a multiplicity of longitudinal adhesive bands 30 of hot-melt adhesive are applied along the full length of the backsheet 16 generally parallel to the longitudinal centerline 70 of the backsheet 16. The longitudinal adhesive bands 30 serve to affix the topsheet 12 to the backsheet 16 at those points where these three components come together. The extent and location of the points where the topsheet 12, backsheet 16, and longitudinal adhesive bands 30 come together will depend on the spacing between the longitudinal adhesive bands 30 and on the distance the topsheet 12 and the backsheet 16 extend beyond the absorbent means 14. The number of longitudinal adhesive bands 30 and the spacing therebetween should be sufficient to securely bond the topsheet 12 to the backsheet 16 in the area between the periphery 20 and the edge of the absorbent means 14.

A hot-melt adhesive suitable for use as longitudinal adhesive bands 30 is manufactured by Eastman Chemical Products Company, of Kingsport, Tenn. and marketed under the tradename Eastobond A-3. It will be noted that the above described manner of affixing the topsheet 12 to the backsheet 16 causes the topsheet 12 to be affixed to the backsheet 16 intermittently along the first and second ends, 22 and 24. The absorbent means 14 is thereby encased between the topsheet 12 and the backsheet 16. Of course, many alternative methods of affixing the topsheet 12 to the backsheet 16 may be used with satisfactory results. For example, the topsheet 12 may be affixed to the backsheet 16 indirectly rather than directly as shown in FIG. 1. Thus, an intermediate member may be used to affix the topsheet 12 to the backsheet 16.

The diaper 10 has a first region 41 and a second region 43 divided by a latitudinal centerline 31. The diaper 10 also has a crotch portion 46 which coextends with part of the first region 41 and the second region 43, and which comprises that portion of the diaper 10 which, when worn, is positioned between the legs of the wearer. A longitudinal centerline 70 divides the diaper 10 into a first longitudinal side 26 and a second longitudinal side 28. The first and second regions 41 and 43 are also provided with first and second laterally spaced portions 45a and 45b which comprise portions of the first and second longitudinal sides 26 and 28.

The absorbent means 14 may be any means which is generally compressible, conformable, non-irritating to the wearer's skin, and which is capable of absorbing and retaining liquids. A preferred absorbent means 14 has first and second opposed faces 32 and 34, respectively, and comprises an absorbent layer 36 and first and second tissue layers 38 and 40, respectively. The first and second tissue layers 38 and 40 overlay the major surfaces of the absorbent layer 36 to form the first and second opposed faces 32 and 34 of the absorbent means 14.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent layer 36 such as a multiplicity of plies of creped cellulose wadding, absorbent foams or sponges, or any equivalent material or combination of materials. The total absorbent capacity of the absorbent layer 36 should, however, be compatible with the design liquid loading in the intended use of the disposable diaper 10. Further, the size and absorbent capacity of the absorbent layer 36 may be varied to accommodate wearers ranging from infants through adults.

The preferred embodiment of diaper 10 illustrated in FIGS. 1 and 2 has an hourglass shaped absorbent layer 36, and is intended to be worn by infants ranging in weight from about 12 to about 26 pounds (about 5 kgs. to about 12 kgs.) The absorbent layer 36 is, therefore, a batt of airfelt approximately 16 inches (41 cm) long when measured along the longitudinal centerline, approximately 12 inches (32 cm) across the first and second ends 22 and 24, and approximately 4 inches (10 cm) across the narrowest part of the crotch portion 46. The absorptive capacity of the airfelt used for the absorbent layer 36 is sufficient to absorb and retain from about 8 to about 16 grams of water per gram of absorbent matrial. Accordingly, the airfelt used in the preferred embodiment shown in FIGS. 1 and 2 weighs from about 30 to about 56 grams and has a generally uniform caliper. It should be understood, however, that the size, shape, configuration, and total absorbent capacity of the absorbent layer 36 may be varied to accommodate wearers ranging from infants through adults. Therefore, the dimensions, shape, and configuration of the absorbent layer 36 may be varied (e.g. the absorbent layer 36 may have a varying caliper, or a hydrophilic gradient, or may contain polymeric gelling agents).

The first and second tissue layers, 38 and 40, are intended to improve the tensile strength of the absorbent core 14 and to reduce the tendency of the absorbent layer 36 to split, lump or ball when wetted. The first and second tissue layers, 38 and 40, also help to improve lateral wicking of liquids, thereby providing a more even distribution of liquid in the absorbent layer 36. While a number of materials and manufacturing techniques may be used to manufacture the first and second tissue layers, 38 and 40, satisfactory results have been obtained with sheets of tissue paper having a basis weight of approximately 10 pounds per 3000 square feet (16 gms per square meter) and having an air permeability of approximately 100 cubic feet per minute per square foot (30 cubic meters per minute per square meter) over a 0.5 inch (13 mm) water pressure drop. While the first and second tissue layers, 38 and 40, are preferably coterminous with the absorbent layer 36, they may have different dimensions, a different configuration, or they may be omitted entirely.

The absorbent means 14 is superimposed on the backsheet 16 and is preferably affixed thereto by any means as is well known in the diaper art. For example, the absorbent core 14 may be secured to the backsheet 16 by a uniform continuous layer of adhesive, a patterned layer of adhesive, or an array of line or spots of adhesive. In the preferred embodiment illustrated in FIGS. 1 and 2 the longitudinal adhesive bands 30 are used to affix the absorbent core 14 to the backsheet 16.

The backsheet 16 is impermeable to liquids and prevents liquids absorbed by the absorbent means 14 from wetting the undergarments, clothing, bedding, and other objects which contact the wearer of the disposable diaper 10. Preferably the backsheet 16 is a polyethylene film of from about 0.0005 to about 0.002 inches (about 0.012 to about 0.051 mm) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent means 14 while still preventing liquid from passing through the backsheet 16.

In a preferred embodiment, the backsheet 16 has a modified hourglass shape extending beyond the absorbent layer 36 a minimum distance of at least from about 0.5 to about 1.0 inch (about 1.3 cm to about 2.5 cm) around the entire diaper periphery 20. The marginal portion 48 is that portion of the diaper 10 between the diaper periphery 20 and the edge of the absorbent layer 36 and comprises longitudinal marginal portions 50 adjacent first and second longitudinal edges 26 and 28, respectively, in the crotch portion 46.

The topsheet 12 is compliant, soft feeling, and non-irritating to the wearer's skin and prevents the wearer of the diaper 10 from contacting the absorbent core 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polypropylene), or a combination thereof. Alternatively, the topsheet 12 may be a foam, such as the reticulated foams which are well known in the art or any of the formed films which are also well known in the art.

A particularly preferred topsheet 12 is a non-woven fabric comprising staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 0.625 inches (15.9 mm).

Clearly there are a number of manufacturing techniques which may be used to manufacture the topsheet 12. For example, the topsheet 12 may be woven, non-woven, spunbonded, carded, or the like. A preferred topsheet 12 is carded, and thermally bonded by means well known to those skilled in the nonwoven fabrics art. Preferably the topsheet 12 has a weight of from about 18 to about 25 grams per square year, a minimum dry tensile strength of at least about 400 grams per centimeter in the machine direction and a wet tensile strength of at least about 55 grams per centimeter in the cross machine direction.

The elastic members 18 are affixed to the diaper 10 along both longitudinal marginal portions 50 so that they tend to draw and hold the diaper 10 against the legs of the wearer. Thus, when worn the diaper 10 will have elasticized leg openings. While this result may be accomplished by any of several means as are well known in the diaper art, a particularly preferred diaper construction incorporating elastic strips is described in detail in the hereinbefore referenced U.S. Pat. No. 3,860,003. In addition, a method and apparatus suitable for manufacturing a disposable diaper having elastic leg bands are described in U.S. Pat. No. 4,081,301 entitled "Method and Apparatus for Continuously Attaching Discrete, Stretched Elastic Strands to Predetermined Isolated Portions of Disposable Absorbent Products", which issued to K. B. Buell on Mar. 28, 1978 and which patent is incorporated herein by reference.

Relating the teachings of U.S. Pat. No. 3,860,003 to the preferred embodiment shown in FIGS. 1 and 2, it can be seen that elastic members 18 are operatively associated with both longitudinal marginal portions 50 in the crotch portion 46 in an elastically contractible condition so that in a normally unrestrained configuration the elastic members 18 effectively contract or gather the longitudinal marginal portions 50.

As used herein the term "operatively associated with" refers to two or more components which act together. In the preferred embodiment shown in FIGS. 1 and 2, the elastic members 18 are operatively associated with both longitudinal marginal portions 50 in the crotch portion 46. Thus, the elastic members 18 are affixed to the longitudinal marginal portions 50 so as to cause the longitudinal marginal portions 50 in the crotch portion 46 to be contracted or gathered.

In the preferred embodiment illustrated the elastic members 18 are affixed to a portion of the backsheet 16 in the longitudinal marginal portions 50. A suitable adhesive will be flexible and of sufficient adhesiveness to hold the elastic member 18 to the backsheet 16 while the elastic member 18 is stretched. An adhesive which has been used with satisfactory results is manufactured by Century Adhesives Corporation of Columbus, Ohio and is marketed under the tradename Century 5227.

The elastic members 18 can be operatively associated with the longitudinal marginal portions 50 in a elastically contractible condition in at least two ways. For example, the elastic member 18 may be stretched and while in the stretched condition affixed to the uncontracted and unstretched longitudinal marginal portions 50. Alternatively, the longitudinal marginal portions 50 may be contracted (e.g., by pleating) and then affixing the unstretched elastic member 18 to the contracted longitudinal marginal portions 50.

A suitable elastic member 18 may be manufactured from a wide variety of elastic materials such as natural rubber, or elastomeric films such as krayton, ethylene propylene monomer, and polyurethane.

In addition, the elastic member 18 may take a multitude of configurations. For example, the width of the elastic members 18 may be varied from about 0.0015 inches to 1.0 inches or more; the elastic member 18 may comprise a single strip of elastic material or may comprise several parallel or non parallel strips of elastic material; or the elastic member 18 may be rectilinear or curvilinear. Still further, the elastic member 18 may be affixed to the diaper 10 in any of several ways which are well known in the art. For example, the elastic members 18 may be ultrasonically bonded or heat sealed into the diaper using a variety of bonding patterns or the elastic members 18 may simply be glued to the diaper 10.

One material which has been found to work well as an elastic member 18 is an elastic tape having a cross section of 0.007 inches by 0.25 inches and which is manufactured from natural rubber. Such a product is marketed by Easthampton Rubber Thread Company under the tradename L-1900 rubber compound. The preferred elastic member 18 produces a tensile force of about 100 grams when stretched 100 percent from its relaxed condition.

The diaper 10 is provided with a fastening means 54 for maintaining the first and second regions 41 and 43 in an overlapping configuration when the diaper 10 is worn. Thus, the diaper 10 is fitted to the wearer and a closure around the waist of the wearer is formed utilizing the fastening means. In a preferred embodiment, the first laterally spaced portion 45a of the first region 41 is fastened to the second region 43 at a first attachment area 47a, and the second laterally spaced portion 45b of the first region is fastened to the second region 43 at a second attachment area 47b.

In a preferred diaper configuration, as in FIG. 1 and 2, the diaper 10 has first and second waist regions 42 and 44 extending, respectively, from the first end 22 and the second end 24 of the diaper periphery 20 toward the lateral centerline 31 of the diaper 10 a distance from about ¼ to about ⅓ the length of the diaper. Thus, the first waist region 42 is a part of the first region, and further encompasses portions of the first and second laterally spaced portions 45a and 45b of the first region 41. Correspondigntly, the second waist region 44 is a part of the second region 43 and further encompasses portions of the first and second laterally spaced portions 45c and 45d of the second region 43. Preferably, the second waist region 44 is utilized as the attachment areas 47a and 47b. Thus, the fastening means 54 affixes the first and second laterally spaced portions 45a and 45b of the waist region 42 first region 41 to the first and second attachment areas 47a and 47b located at the second waist region 44 of the second region 43.

The fastening means 54 must be affixed to the first region 41 and the second region 43 in a manner and with a strength that is sufficient to resist the forces acting to cause the first and second regions 41 and 43 to separate during wearing.

The fastening means 54 may comprise any of the well known means for achieving a waist closure wherein discrete fastener means are utilized on each side of the centerline. Such fastener means include hook and pile fasteners and adhesive tape. A preferred fastening means 54 is the adhesive tape 55 as is well known in the diaper art.

Any of the well known configurations and constructions may be used as the adhesive tape 55. For example, the adhesive tape 55 may be a single tape or a multiple use tape (i.e., refastenable). A preferred adhesive tape 55 is a Y-shaped tape as described in detail in U.S. Pat. No. 3,848,594 entitled Tape Fastening System for Disposable Diaper which issued to K. B. Buell on Nov. 19, 1974, which patent is incorporated herein by reference. The fastening means 54 are provided at both the first and second longitudinal sides, 26 and 28 respectively.

The preferred adhesive tape 55 illustrated in FIG. 2 has a proximal end 56 and a distal end 58. The proximal end 56 is that end of the adhesive tape 55 which the proximal end of the diaper 10 affixes to the diaper 10 while the distal end 58 is that end of the adhesive tape 55 which the user affixes to the diaper 10 when fitting the diaper 10 to the wearer. The proximal end 56 is affixed to the first waist portion 42 and after fitting the diaper 10 about the waist of the wearer the distal end 58 is affixed to the second waist portion 44 thereby causing the diaper 10 to encircle the waist of the wearer and effecting a waist closure.

The second waist portion 44 has panels 62. The panels 62 are those portions of the second waist portion 44 which are overlain by the first waist portion 42 when the diaper 10 is fastened about the waist of the wearer. The extent to which the second waist portion 44 is overlain and thus the extent to which panels 62 are formed will depend on the overall dimensions and shape of the diaper 10 and the size of the wearer.

As described hereinabove, the diaper is fitted to the wearer so that the diaper 10 conforms to the wearer's waist and legs. However in fitting the diaper 10 to the wearer, especially infants, it can be difficult to affix the fastening means 54 located on each side of the centerline 70 to precisely optimum or desired locations. The result is inconsistent and often improper diaper fit lending to diaper leakage and/or irritation due to excessively tight fit.

According to the present invention, and referring to the prepared embodiments shown in FIGS. 1 and 2, the indicia 72 and 74 are provided on the second region 43 of the backsheet 16 of the diaper 10 in areas at least coextensive with a part of the first and second attachment areas 47a and 47b. The indicia are positioned such that they may guide the individual fitting the diaper to (1) affix a first fastening 54 means on the first longitudinal side 26 of the longitudinal centerline 70 to a predetermined position on the first attachment area 47a and (2) after having affixed said first fastening 54 means, to affix the fastening means 54 on the second longitudinal side 28 of the centerline 70 to a predetermined position of the second attachment area 47b. Preferably, the indicia are designed so that the position of the second-affixed fastening means 54 can be readily determined by examining the position of affixation of the first-affixed fastening means 54 relative to the corresponding indicia 72 and 74. As an alternative or concurrent embodiment, the indicia may be positioned to provide guidance in positioning the waist regions of the diaper in conjunction with affixation of the fastening means to the diaper. Thus, referring to FIGS. 1 and 2, it can be seen that the periphery 20 of the first waist diaper 10 portion 42 can be placed at particular desired locations relative to the indicia 72 and 74.

The indicia may comprise any visual form which facilitates the individual fitting the diaper to affix the fastening tabs at predetermined, corresponding locations. Without limiting the scope of the invention, the indicia may comprise patterns, symbols, ornamental designs, script, color codings, or other markings. It is additionally contemplated to utilize combinations of forms of indicia. Thus, in a preferred embodiment, the indicia 72 and 74 are provided with identifying markings such as symbols, ornamental designs or script. In the specific example shown in FIG. 1, the vertical line indicia 73 and 75 have identifying markings 76 and 78, in the form of dots, located at varying identifying positions on the vertical lines 73 and 75. For each vertical line 73 having a marking 76 at a particular identifying position on the first longitudinal side 26, there is a corresponding vertical line 75 on the second longitudinal side 28 of the centerline 70 having a marking 78 at a corresponding identifying position. The vertical line indicia 73 and 75 provide guidance for horizontal positioning of the fastening means and/or first waist portion 42. The markings 76 and 78 provide further guidance to the individual fitting the diaper by facilitating the individual's ability to initially choose a desired fastening location for a first attached fastening means 54 based on experience and to promptly choose the corresponding attachment location for a second fastening means 54. In the practice of the preferred embodiment, the individual would affix the second fastening means 54 at a position proximate to the vertical line of the indicia 75 having the identifying marking 78 which corresponds to the vertical line, having a similarly situated marking 76, of the indicia 73 at a position proximate to the position of the first attached attachment means 54. Additionally, the vertical line indicia 76 and 78 inherently provide guidance in choosing the preferred vertical attachment position for the fastening means 54. The individual fitting the diaper may determine an approximate vertical position by examining the position of the fastening means 54 relative to a particular vertical line of the indicia 73 and 75, thereby resulting in more consistent fit for subsequently fitted diapers. Such indicia which have similar identifying corresponding positions for markings at each set of indicia to thereby aid in coordinating optimum waist fit and leg opening fit shall be referred to as position coded indicia.

An alternative preferred embodiment is shown in FIG. 2, wherein the indicia 72 and 74 comprise a plurality of horizontally and vertically arranged discrete circular markings 80 and 82. The vertically arranged discrete markings enhance the degree of guidance in affixing the fastening means to the desired vertical attachment position.

Referring to FIG. 3, provided is an expanded view of a set of indicia 74 wherein vertical rows 83 of discrete circular markings 82 are color coded. Color coding of the indicia 74, in conjunction with corresponding color coding for each particular vertical row 83 of indicia 72 on the opposing side of the centerline 70, provides additional guidance in ascertaining the desired horizontal fastening locations in a manner analogous to the benefit imparted by the identifying markings 76 and 78 of FIG. 1. Such indicia shall be referred to as color coded indicia.

In other alternative preferred embodiment, it will be apparent to one skilled in the art that the indicia 72 and 74 of FIG. 1, 2, or 3 may analogously be varying in shape rather than, or in addition to varying in color or having identifying markings. Such indicia which are varying in shape shall also be referred to as position coded indicia.

The diapers shown in FIGS. 1 and 2 are preferred diaper embodiments which are substantially symmetrical about the longitudinal centerline 10. The indicia 72 and 74 and positioning of the additional indicia markings 76 and 78 of FIG. 1 and the color coding of the vertical rows of markings 80 and 82 are also substantially symmetrically oriented about the longitudinal centerline 70 in the preferred embodiments. In practice, the fastening means 54 are affixed to the attachment areas 47a and 47b at approximately equidistant positions from the centerline 70.

Whereas corresponding identifying markings are preferred, it should be understood that the present development is applicable to indicia, such as shown in FIG. 1, without additional identifying markings. This invention is also applicable to indicia having identifying markings which do not correspond in position, color or other mode of comparison such as shown in FIGS. 1 and 3. Also, whereas substantially symmetrical orientation of the diaper and indicia is preferred, the present invention is also applicable to unsymmetrical orientations of the diaper and the indicia. In such cases, the indicia may facilitate proper fitting of the diaper based upon the experience of the individual fitting the diaper in conjunction with the ability of that individual to remember and repeat preferred or optimal fastening locations relative to the indicia.

The indicia 72 and 74 are applied to the diaper 18 in a manner such that the indicia 72 and 74 are discernible to an individual while fitting the diaper to wearer. Preferably, the indicia 72 and 74 may be applied directly on the backsheet 16 of the diaper 10 by printing with such materials as visually observable ink, glue or polymeric compounds or by extruding with such materials as visually observable glue or polymeric compounds. Also preferably, the indicia 72 and 74 may be printed on a separate sheet which is then adhered to the backsheet 16 with a suitable adhesive compound.

The preferred embodiments disclosed herein are not intended to limit the scope of this invention. The scope of the invention, including but not limited to the preferred embodiments described herein, is defined by the following claims,

What is claimed is:

1. An absorbent article having a liquid pervious topsheet, a liquid impervious backsheet attached to said topsheet and an absorbent medium disposed between said topsheet and said backsheet, said article comprising:
   a. a first region having first laterally spaced portion and a second laterally spaced portion;
   b. a second region connected to said first region;
   c. fastening means for fastening said first laterally spaced portion of said first region to said second region at a first attachment area;
   d. fastening means for fastening said first second laterally spaced portion of said first region to said second region at a second attachment area;
   e. indicia means coextensive with at least a part of said first attachment area; and
   f. indicia means coextensive with at least a part of said second attachment area; said indicia means providing guidance in fitting said article to a wearer.

2. An absorbent article as described in claim 1, wherein said fastening means described in (c) and said fastening means described in (d) each comprise at least one fastening tab having a proximal end attached to said first region and a distal end disposed to fasten to said second region.

3. An absorbent article as described in claim 2, wherein said fastening means described in (c) and (d) comprise adhesive tape fastening tabs.

4. An absorbent article as described in claim 3, wherein said distal end of said adhesive tape fastening tabs are disposed to fasten to said backsheet of said second region.

5. An absorbent article as described in claim 1, wherein said article further comprises a longitudinal centerline extending from said first region to said second region, wherein said first attachment area is located on a first longitudinal side of said centerline and said second attachment area being located on a second longitudinal side of said centerline.

6. An absorbent article as described in claim 5, wherein said article is substantially longitudinally symmetrical about said longitudinal centerline, said indicia means described in (e) being located on the first longitudinal side of said centerline and said indicia menas described in (f) being located on the second longitudinal side of said longitudinal centerline.

7. An absorbent article as described in claim 6, wherein said indicia means described in (e) and (f) are substantially symmetrically disposed about said longitudinal centerline.

8. An absorbent article as described in claim 7, wherein said indicia means described in (e) and (f) comprise a plurality of vertical lines.

9. An absorbent article as described in claim 8, wherein said plurality of vertical lines are varying in color.

10. An absorbent article as in claim 9, wherein said indicia means are color coded.

11. An absorbent article as described in claim 7, wherein said indicia means described in (e) and (f) comprise a plurality or vertically and horizontally arranged rows of discrete markings.

12. An absorbent article as described in claim 11, wherein the vertical rows of said indicia means described in (e) and (f) are varying in color.

13. An absorbent article as described in claim 8, wherein said indicia means further comprise identifying markings.

14. An absorbent article as described in claim 13, wherein said indicia means are position coded.

15. An absorbent article as described in claim 12, wherein said indicia means are color coded.

16. An absorbent article as described in claim 11, wherein said indicia means are position coded.

17. An absorbent article as described in claim 1, further comprising a separate sheet, said indicia means being positioned on said separate sheet, and said separate sheet being attached to said backsheet.

18. An absorbent article as described in claim 1, further comprising a first separate sheet, said indicia means being positioned on said first separate sheet, said first separate sheet being attached to at least a part of said first attachment area, and a second separate sheet, said indicia means being positioned on said second separate sheet and said second separate sheet being attached to at least a part of said second attachment area.

* * * * *

UNITED STATES PATENT AND TRADEMARK OFFICE
CERTIFICATE OF CORRECTION

PATENT NO. : 4,662,875
DATED : May 5, 1987
INVENTOR(S) : Dennis O. Hirotsu, Anthony J. Robertson It is certified that error appears in the above-identified patent and that said Letters Patent is hereby corrected as shown below:

Column 6, line 50, "year" should read --yard--.

Column 8, line 18, "Correspondignly," should read --correspondingly,"

Column 11, line 35, "said indicia means..." should be a new paragraph under 1.

Signed and Sealed this

Seventeenth Day of March, 1992

Attest:

HARRY F. MANBECK, JR.

*Attesting Officer*  *Commissioner of Patents and Trademarks*

REEXAMINATION CERTIFICATE (1043rd)
United States Patent [19]
Hirotsu et al.

[11] B1 4,662,875
[45] Certificate Issued  Apr. 18, 1989

[54] ABSORBENT ARTICLE

[75] Inventors: Dennis O. Hirotsu, Cincinnati, Ohio; Anthony J. Robertson, Madison, Wis.

[73] Assignee: The Procter & Gamble Company, Cincinnati, Ohio

Reexamination Reqs:st:
No. 90/001,309, Aug. 17, 1987
No. 90/001,346, Oct. 8, 1987

Reexamination Certificate for:
Patent No.: 4,662,875
Issued: May 5, 1987
Appl. No.: 802,803
Filed: Nov. 27, 1985

[51] Int. Cl.⁴ ............................................. A61F 13/16
[52] U.S. Cl. ...................................................... 604/389
[58] Field of Search .............. 604/389, 390, 391, 394, 604/396, 385.1, 385.2; 128/165, DIG. 15

[56] References Cited
U.S. PATENT DOCUMENTS

| | | | |
|---|---|---|---|
| 3,081,772 | 4/1960 | Brooks | 604/391 |
| 3,638,651 | 2/1972 | Torr | 604/390 |
| 3,646,937 | 3/1972 | Gellert | 604/390 |
| 3,856,008 | 12/1974 | Fowler et al. | 128/DIG. 15 |
| 3,869,761 | 3/1975 | Schaar | 604/390 |
| 4,036,233 | 8/1977 | Kozak | 604/389 |

FOREIGN PATENT DOCUMENTS

| | | |
|---|---|---|
| 080647 | 6/1983 | European Pat. Off. |
| 1263391 | 11/1972 | Fed. Rep. of Germany ...... 128/169 |
| 2122164 | 12/1961 | France ................................ 604/389 |
| 1095397 | 12/1967 | United Kingdom . |
| 2135568A | 9/1984 | United Kingdom . |

*Primary Examiner*—John D. Yasko

[57] ABSTRACT

An absorbent article, such as a disposable diaper or an incontinent brief having indicia means provided for aiding an individual fitting the article to a wearer to obtain optimal waist fit and leg opening fit. Indicia means are provided in an area at least coextensive with a part of an area to which fastening means are affixed to the article when the article is fitted to a wearer. Indicia, as used herein are any type of lines, patterns, ornamental designs, symbols, script, color codes, or other markings which have the capability, either inherently or with additional denotation, to aid an individual fitting the article to promptly locate a desired affixation point for a particular fastening means.

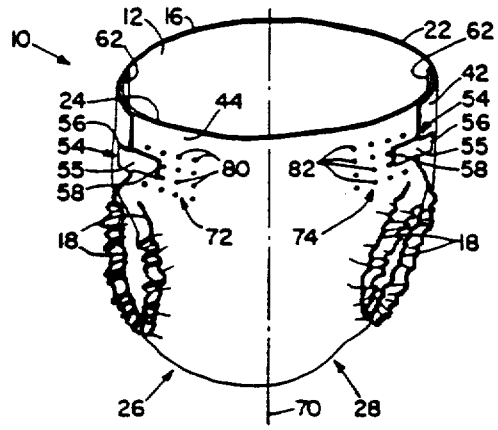

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5–7 are cancelled.

Claims 1, 2, 8, 11, 12, 14, 17 and 18 are determined to be patentable as amended.

Claims 3, 4, 9, 10, 13, 15 and 16, dependent on an amended claim, are determined to be patentable.

New claim 19 is added and determined to be patentable.

1. An absorbent article having a liquid pervious topsheet, a liquid impervious backsheet attached to said topsheet, and an absorbent medium disposed between said topsheet and said backsheet, said article comprising:
   a. a first region having *a* first laterally spaced portion and a second laterally spaced portion;
   b. a second region connected to said first region;
   c. fastening means for fastening said first laterally spaced portion of said first region to said second region at a first attachment area;
   d. fastening means for fastening said second laterally spaced portion of said first region to said second region at a second attachment area;
   e. indicia means *comprising a plurality of discrete markings* coextensive with at least a part of said first attachment area; [and]
   f. indicia means *comprising a plurality of discrete markings* coextensive with at least a part of said second attachment area; *and*
   g. *a longitudinal centerline extending from said first region to said second region;*
   wherein said indicia means described in (e) and (f) comprise a plurality of horizontal arranged rows of discrete markings that are substantially symmetrically disposed about said longitudinal centerline, said indicia means providing guidance for horizontal and vertical positioning in fitting said article to a wearer.

2. An absorbent article as described in claim 1 *or 19*, wherein said fastening means described in (c) and said fastening means described in (d) each comprise at least one fastening tab having a proximal end attached to said first region and a distal end disposed to fasten to said second region.

8. An absorbent article as described in claim [7] *1*, wherein said indicia means described in (e) and (f) comprise a plurality of vertical lines.

11. An absorbent article as described in claim [7] *1*, wherein said indicia means described in (e) and (f) comprise a plurality of vertically and horizontally arranged rows of discrete markings.

12. An absorbent article as described in claim 11 *or 19*, wherein the vertical rows of said indicia means described in (e) and (f) are varying in color.

14. An absorbent article as described in claim 13 *or 19*, wherein said indicia means are position coded.

17. An absorbent article as described in claim 1 *or 19*, further comprising a separate sheet, said indicia means being positioned on said separate sheet, and said separate sheet being attached to said backsheet.

18. An absorbent article as described in claim 1 *or 19*, further comprising a first separate sheet, said indicia means being positioned on said first separate sheet, said first separate sheet being attached to at least a part of said first attachment area, and a second separate sheet, said indicia means being positioned on said second separate sheet and said second separate sheet being attached to at least a part of said second attachment area.

*19. An absorbent article having a liquid pervious topsheet, a liquid impervious backsheet attached to said topsheet, and an absorbent medium disposed between said topsheet and said backsheet, said article comprising:*
   *a. a first region having a first laterally spaced portion and a second laterally spaced portion;*
   *b. a second region connected to said first region;*
   *c. fastening means for fastening said first laterally spaced portion of said first region to said second region at a first attachment area;*
   *d. fastening means for fastening said second laterally spaced portion of said first region to said second region at a second attachment area;*
   *e. indicia means coextensive with at least a part of said first attachment area;*
   *f. indicia means coextensive with at least a part of said second attachment area; and*
   *g. a longitudinal centerline extending from said first region to said second region;*
   *wherein said indicia means described in (e) and (f) comprise a plurality of vertically and horizontally arranged rows of discrete markings, said indicia means providing guidance for horizontal and vertical positioning in fitting said article to a wearer.*

* * * * *